(12) United States Patent
Augello et al.

(10) Patent No.: US 6,500,462 B1
(45) Date of Patent: *Dec. 31, 2002

(54) EDIBLE MCC/PGA COATING COMPOSITION

(75) Inventors: Michael Augello, Marlboro, NJ (US); Sheila M. Dell, New Hope, PA (US); Eric H. Bliefernich, Yardville, NJ (US)

(73) Assignee: FMC Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/696,780

(22) Filed: Oct. 26, 2000

Related U.S. Application Data

(60) Provisional application No. 60/217,499, filed on Jul. 11, 2000, provisional application No. 60/189,588, filed on Mar. 15, 2000, provisional application No. 60/172,526, filed on Dec. 17, 1999, provisional application No. 60/167,407, filed on Nov. 24, 1999, and provisional application No. 60/162,514, filed on Oct. 29, 1999.

(51) Int. Cl.⁷ ............... A61K 9/16; A61K 9/14; A61K 9/20
(52) U.S. Cl. ............. 424/490; 424/464; 424/489; 424/493; 424/494; 424/496
(58) Field of Search ............... 424/464, 489, 424/490, 493, 494, 496

(56) References Cited

U.S. PATENT DOCUMENTS

| | | |
|---|---|---|
| 2,881,085 A | 4/1959 | Endicott et al. |
| 3,297,535 A | 1/1967 | Butler et al. |
| 3,438,797 A | 4/1969 | Biddle, Sr. |
| 3,503,769 A | 3/1970 | McDowell ............... 106/208 |
| 3,649,302 A * | 3/1972 | Daggy et al. ............ 99/139 |
| 3,851,574 A | 12/1974 | Katz et al. |
| 3,860,733 A | 1/1975 | Morse et al. |
| 3,873,694 A | 3/1975 | Kanig |
| 3,883,458 A | 5/1975 | Mueller et al. ........ 260/28.5 R |
| 3,906,086 A | 9/1975 | Guy et al. |
| 3,935,326 A | 1/1976 | Groppenbacher et al. |
| 3,957,966 A | 5/1976 | Valan |
| 4,060,598 A | 11/1977 | Groppenbacher et al. |
| 4,095,992 A | 6/1978 | Rudolph et al. |
| 4,112,215 A | 9/1978 | Boessler et al. |
| 4,143,163 A | 3/1979 | Hutchinson et al. |
| 4,274,830 A | 6/1981 | Woznick et al. |
| 4,307,117 A | 12/1981 | Leshik ............... 426/96 |
| 4,316,884 A | 2/1982 | Alam et al. |
| 4,336,244 A | 6/1982 | Woznick et al. |
| 4,340,582 A | 7/1982 | Kriesel et al. |
| 4,432,966 A | 2/1984 | Zeitoon et al. |
| 4,505,890 A | 3/1985 | Jain et al. |
| 4,514,384 A | 4/1985 | Gallina |
| 4,533,562 A | 8/1985 | Ikegami et al. |
| 4,576,646 A | 3/1986 | Branco et al. |
| 4,645,662 A | 2/1987 | Nakashima et al. ......... 424/52 |
| 4,661,162 A | 4/1987 | Kurihara et al. |
| 4,666,703 A | 5/1987 | Kopf |
| 4,693,750 A | 9/1987 | Bauer et al. |
| 4,784,858 A * | 11/1988 | Ventouras ............ 424/468 |
| 4,790,881 A | 12/1988 | Wittwer et al. |
| 4,792,452 A | 12/1988 | Howard et al. |
| 4,802,924 A * | 2/1989 | Woznicki et al. .......... 427/3 |
| 4,877,629 A | 10/1989 | Stypula et al. |
| 4,900,557 A * | 2/1990 | Dell et al. ............ 424/452 |
| 4,959,227 A | 9/1990 | Amer ................ 426/35 |
| 4,983,399 A | 1/1991 | Maish |
| 4,994,276 A | 2/1991 | Baichwal et al. ......... 424/440 |
| 5,008,117 A | 4/1991 | Calanchi et al. |
| 5,023,083 A | 6/1991 | Drell ................ 424/439 |
| 5,068,110 A | 11/1991 | Fawzi et al. |
| 5,128,143 A | 7/1992 | Baichwall et al. ........ 424/464 |
| 5,194,464 A | 3/1993 | Itoh et al. |
| 5,202,137 A | 4/1993 | Duffy et al. |
| 5,209,942 A | 5/1993 | Bauer et al. ........... 426/605 |
| 5,225,202 A | 7/1993 | Hodges et al. |
| 5,262,173 A | 11/1993 | Sheth et al. ........... 424/494 |
| 5,268,182 A | 12/1993 | Brinker et al. |
| 5,286,510 A | 2/1994 | Bauer et al. ........... 426/573 |
| 5,288,501 A | 2/1994 | Nurnberg et al. |
| 5,306,506 A | 4/1994 | Zema et al. |
| 5,332,595 A * | 7/1994 | Gaonkar ............... 426/602 |
| 5,368,840 A | 11/1994 | Unger ................. 424/9 |

(List continued on next page.)

FOREIGN PATENT DOCUMENTS

| | | |
|---|---|---|
| DE | 2820981 | 4/1979 |
| EP | 0063014 | 8/1985 |
| EP | 0153104 | 8/1985 |
| EP | 0 171 457 | 2/1986 |
| EP | 0 181 650 | 5/1986 |
| EP | 0020496 | 1/1988 |
| EP | 0 255 725 | 2/1988 |
| EP | 0256538 | 2/1988 |

(List continued on next page.)

OTHER PUBLICATIONS

PCT/US00/29849 Search Report dated Jan. 25, 2001.
"A clear advance in convential coatings," Introducing Lustre Clear™ Microcrystalline Cellulose/Carrageenan–Based Coating System brochure, *FMC BioPolymer*, 1999, 17 pages.

(List continued on next page.)

Primary Examiner—Thurman K. Page
Assistant Examiner—S. Tran
(74) *Attorney, Agent, or Firm*—Woodcock Washburn LLP

(57) ABSTRACT

An edible, hardenable coating composition is disclosed containing microcrystalline cellulose, a film forming amount of propylene glycol alginate, and a strengthening polymer, optionally in combination with at least one of a plasticizer, a surfactant, or a filler. The coating composition of the present invention may be applied to pharmaceutical and veterinary solid dosage forms, confectionery, seeds, animal feed, fertilizers, pesticide tablets, and foods and provides an elegant prompt release coating which does not retard the release of active ingredients from the coated substrate.

20 Claims, No Drawings

U.S. PATENT DOCUMENTS

| | | | |
|---|---|---|---|
| 5,411,746 A | 5/1995 | Signorino et al. | |
| 5,435,840 A | 7/1995 | Hilborn | |
| 5,458,887 A | 10/1995 | Chen et al. | |
| 5,470,603 A | 11/1995 | Staniforth et al. | |
| 5,472,710 A | 12/1995 | Klokkers-Bethke et al. | |
| 5,472,712 A | 12/1995 | Oshlack et al. | 424/480 |
| 5,512,314 A | 4/1996 | Signorino et al. | |
| 5,514,435 A | 5/1996 | Suzuki et al. | 428/40 |
| 5,523,293 A | 6/1996 | Jane et al. | 514/21 |
| 5,529,783 A | 6/1996 | Burke et al. | 424/441 |
| 5,580,580 A | 12/1996 | Masterson et al. | 424/490 |
| 5,595,762 A | 1/1997 | Derrieu et al. | |
| 5,656,080 A | 8/1997 | Staniforth et al. | |
| 5,662,732 A | 9/1997 | Kelley et al. | |
| 5,683,722 A | 11/1997 | Derrieu et al. | |
| 5,695,784 A | 12/1997 | Pollinger et al. | |
| 5,700,929 A | 12/1997 | Kokubo et al. | |
| 5,709,896 A | 1/1998 | Hartigan et al. | 426/103 |
| 5,733,575 A | 3/1998 | Mehra et al. | |
| 5,741,600 A | 4/1998 | Olson | |
| 5,759,576 A | 6/1998 | Barcomb | |
| 5,759,577 A | 6/1998 | Barcomb | |
| 5,780,057 A | 7/1998 | Conte et al. | 424/468 |
| 5,840,332 A | 11/1998 | Lerner et al. | |
| 5,849,320 A | 12/1998 | Turnblad et al. | |
| 5,851,579 A | 12/1998 | Wu et al. | |
| 5,876,739 A | 3/1999 | Turnblad et al. | |
| 5,882,707 A | 3/1999 | Grillo | |
| 5,885,617 A | 3/1999 | Jordan | |
| 6,153,601 A | 11/2000 | Breton et al. | |
| 6,228,398 B1 * | 5/2001 | Devane et al. | 424/484 |
| 6,274,162 B1 | 8/2001 | Steffenino et al. | |

FOREIGN PATENT DOCUMENTS

| | | |
|---|---|---|
| EP | 0305051 | 1/1989 |
| EP | 0339811 | 11/1989 |
| EP | 0 347 748 | 12/1989 |
| EP | 0222856 | 12/1990 |
| EP | 0425154 | 5/1991 |
| EP | 0443572 | 8/1991 |
| EP | 0 453 001 | 10/1991 |
| EP | 0460185 | 12/1991 |
| EP | 525389 | 6/1992 |
| EP | 0497331 | 8/1992 |
| EP | 0527637 | 2/1993 |
| EP | 0550737 | 7/1993 |
| EP | 595110 | 10/1993 |
| EP | 0567541 | 11/1993 |
| EP | 0 600 775 | 6/1994 |
| EP | 0 627 173 | 12/1994 |
| EP | 0 630 646 | 12/1994 |
| EP | 0648487 | 4/1995 |
| EP | 0663820 | 7/1995 |
| EP | 0684042 | 11/1995 |
| EP | 0707475 | 4/1996 |
| EP | 0737472 | 10/1996 |
| EP | 0746310 | 12/1996 |
| EP | 0 795 324 | 9/1997 |
| EP | 0839527 | 5/1998 |
| EP | 0852141 | 7/1998 |
| EP | 1010423 | 6/2000 |
| GB | 734414 | 1/1956 |
| GB | 1594102 | 9/1977 |
| GB | 2 212 396 | 7/1989 |
| JP | 52117413 | 3/1976 |
| JP | 51044624 | 4/1976 |
| JP | 118057 | 5/1982 |
| JP | 5-29205 | 10/1985 |
| JP | 6-62400 | 5/1987 |
| JP | 62-111917 | 5/1987 |
| JP | 2134366 | 3/1995 |
| JP | 2646851 | 5/1997 |
| JP | 11315032 | 11/1999 |
| WO | WO 84/02843 | 8/1984 |
| WO | WO 85/01207 | 3/1985 |
| WO | WO 86/06626 | 11/1986 |
| WO | WO88/01506 | 3/1988 |
| WO | WO 88/03795 | 6/1988 |
| WO | WO9114729 | 10/1991 |
| WO | WO 91/15548 | 10/1991 |
| WO | WO9209273 | 6/1992 |
| WO | WO 92/11002 | 7/1992 |
| WO | WO 92/15288 | 9/1992 |
| WO | WO 94/03160 | 2/1994 |
| WO | WO 95/11667 | 5/1995 |
| WO | WO9528918 | 11/1995 |
| WO | WO9601874 | 1/1996 |
| WO | WO96/10995 | 4/1996 |
| WO | WO 96/29058 | 9/1996 |
| WO | WO 96/33700 | 10/1996 |
| WO | WO 97/15191 | 5/1997 |
| WO | WO9737638 | 10/1997 |
| WO | WO98/17126 | 4/1998 |
| WO | WO9953899 | 4/1998 |
| WO | WO98/20861 | 5/1998 |
| WO | WO9830341 | 7/1998 |
| WO | WO9902135 | 1/1999 |
| WO | WO9908658 | 2/1999 |
| WO | WO9938495 | 8/1999 |
| WO | WO0001370 | 1/2000 |
| WO | WO0126633 | 10/2000 |

OTHER PUBLICATIONS

Supplementary European Search Report for Application No. EP 00 90 7193.

The Use of Carrageenan in Mixture with Microcrystalline Cellulose and its Functionality for Making Tablets., Katharina M. Picker, European Journal of Pharmaceutics and Biopharmaceutics.,48(1), pp. 27–36 (1999).

Leon Lachman, Herbert Lieberman & Joseph Kanig, The Theory and Practice of Industrial Pharmacy, 3rd ed. (Philadelphia, PA.: Lea & Febiger, 1986),pp76–77,321,327–328.

Colliopoulos, J.A., et al., "Rheological properties of microcrystalline cellulose (MCC) carrageenan aqueous film coating," *Annual Meeting*, Nov. 14–18, 1999, AAPS Abstract No. 3480, 1 page.

Dell, S.M., et al., "Evaluation of mechanical properties of free films of aqueous coating systems," *Annual Meeting*, Nov. 14–18, 1999, AAPS Abstract No. 2906, 1 page.

Dell, S.M., et al., "Evaluation of microcrystalline cellulous (MCC): carrageenan mixture as a film former in conventional aqueous film coating," *Annual Meeting*, Nov. 14–18, 1999, AAPS Abstract No. 2925, 1 page.

Lee, J.T., "Evaluation of the functional stability of microcrystalline cellulose (MCC): carrageenan conventional aqueous film coating," *Annual Meeting*, Nov. 14–18, 1999, AAPS Abstract No. 3459, 1 page.

* cited by examiner

EDIBLE MCC/PGA COATING COMPOSITION

RELATED APPLICATIONS

This application claims the benefit of prior Provisional Application No. 60/162,514, filed Oct. 29, 1999, No. 60/167,407, filed Nov. 24, 1999, No. 60/172,526, filed Dec. 17, 1999, No. 60/189,588, filed Mar. 15, 2000, and No. 60/217,499, filed Jul. 11, 2000.

FIELD OF THE INVENTION

This invention relates to edible, hardenable coating compositions comprising microcrystalline cellulose (MCC), a film forming amount of propylene glycol alginate (PGA) and a strengthening polymer, optionally containing a plasticizer, a surface active agent, a filler, a coloring agent or a combination of such optional ingredients. The coatings of the present invention can be applied to pharmaceutical, including neutraceutical, and veterinary solid dosage forms, such solid substrates such as seeds, animal feed, fertilizers, pesticide tablets and granules, and also to confectionery and foods. They are readily dispersed in aqueous media, and, when applied as a coating, provide high lustre coatings, which do not retard or extend release of active ingredient from a coated substrate.

BACKGROUND OF THE INVENTION

It is a common practice to coat pharmaceutical and veterinary tablets to obtain several advantages. Among these are to improve the surface characteristics of tablets to make them easier to swallow, to reduce the absorption of water or moisture which can potentially degrade the active ingredient or promote some other undesirable change in the tablet structure, and simply to make a more elegant appearing tablet.

Another very important function of a pharmaceutical or veterinary tablet coating is to improve the integrity of the tablet itself. Uncoated tablets are often subject to being abraded or chipped, causing a loss of active ingredient in the process. More dramatically, they may break into two or more pieces. One measure of a useful coating is its ability to prevent any of these physical degradations of tablet structure. The effectiveness of a coating material to prevent abrading, chipping, or breakage of the tablet is determined by friability testing.

Confectionery and foods may be coated with a formulation to preserve the confection or food from deteriorating by contact with the oxygen and the moisture in the atmosphere. Coatings also can provide improved appearance and desirable organoleptic properties to the food as well as preventing loss of flavor.

Seeds may be coated to preserve the viability of the seeds by protecting against moisture. They may also be coated as a means for increasing particle size to facilitate mechanical planting. A dye can be included in the coating formulation to identify the seeds as to quality, type, or some other designation. Frequently, a pesticide, e.g., a fungicide, is incorporated into the coating formulation to protect both the seed itself and the seedling that results from germination of the seed. In all cases, this coating must not decrease the viability of the seeds or interfere with germination when the seeds are planted in the soil.

Animal feed may be coated to improve its flowability, appearance and its resistance to powdering or dusting. In such applications, the coating may be formulated to include vitamins, hormones, antibiotics, or the like, to benefit the livestock which will consume the feed.

Fertilizers, in either granular or tableted forms, may be coated to retain the integrity of the form and, especially, to protect the fertilizer from moisture which can cause agglomeration during storage, which could make rapid, even application to the soil difficult or inconvenient.

Coating of tableted pesticide formulations serves to maintain the integrity of the tablets or granules until they are placed in water where they rapidly disintegrate, forming a solution or slurry to be applied to the soil or plants. A second, and equally important, function of the coatings on tablets containing pesticides is to prevent human contact with the pesticide, thereby increasing safety for those handling and applying the pesticide.

In the preparation of a coating formulation to be sprayed, the film-former is usually dissolved or dispersed in a solvent, for example, water, along with the other ingredients of the formulation. In aqueous systems, since many polymers require significant time to become fully hydrated, the coating formulation must frequently be prepared in advance of the time it is to be applied to the tablets. A common procedure is to prepare these coating formulations the day preceding the coating operation in order to assure adequate hydration of the polymers used in them.

A particular disadvantage of coatings based primarily on hydroxypropylmethylcellulose (HPMC) is that the coating may harden over time and therefore increase tablet disintegration times. An increase in disintegration time delays the bioavailability of the active ingredient at least in proportion to the increase in disintegration time. Many other agents commonly used in coating compositions are also known to delay release of pharmaceutical agents, such as enteric coatings which use polymeric film forming materials which are insoluble in water, or gastric fluid, some of these being specifically selected to by-pass both the stomach and small intestine and provide colonic release.

The coatings of this invention meet U.S. Pharmacopeia standards for rapid or immediate dissolution (U.S.P. monograph 23) of active ingredients from tablets or other solid dosage forms coated with them. They provide prompt release or dissolution consistent with the release rates which is normally obtained with the uncoated tablets or other substrates. Thus, they do not adversely impact or retard release of active ingredients from a substrate coated with them. Further, the coatings of this invention are readily dispersed and rapidly hydrated in aqueous media for application to a coating substrate, and provide elegant coatings which have all the benefits of coatings now in commercial use without the drawbacks that are common to them.

SUMMARY OF THE INVENTION

It has been found that these and other advantages may be achieved in accordance with the present invention by a coating composition which comprises a unique combination of materials specifically adapted for prompt release when placed in aqueous media or ingested. The coating composition of the present invention comprises microcrystalline cellulose, a film forming amount of propylene glycol alginate and a strengthening polymer, and may additionally contain a plasticizer, a surface active agent, a filler, a coloring agent or combination of these additional ingredients. More specifically, the present invention provides a prompt release, edible, hardenable coating composition, as well as dry coatings and aqueous dispersions thereof and solid dosage forms coated therewith.

DETAILED DESCRIPTION OF THE INVENTION

For purposes of this application, the term "edible" is intended to mean food grade materials which are approved by regulatory authorities for use in pharmaceutical or food applications. The term "hardenable," used to describe the coating compositions of this invention, is intended to include only those coating compositions that are capable of being dried from an aqueous solution or dispersion thereof into a solid coating which resists abrasive forces, i.e. a hardened coating, as distinguished from those "enrobing" coatings on confections which set up into a soft coating that can be handled and packaged but which do not resist abrasive forces significantly. The terms "immediate," "rapid," or "prompt," as applied to dissolution rates or times for the coating compositions of this invention or tablets coated with the compositions of this invention, mean that the coatings of this invention meet U.S. Pharmacopeia standards (U.S.P. monograph 23) for rapid or immediate dissolution of active ingredients from tablets or other solid dosage forms coated with them. Thus, they provide prompt release or dissolution consistent with the release rates which is normally obtained with the uncoated tablets or other substrate. They do not, when placed in water or ingested, adversely impact or retard release or dissolution of tablets or other dosage forms coated with them. Coatings made in accordance with the present invention are substantially or completely disintegrated and/or dissolved within less than 10 minutes after being ingested or placed in aqueous media. These definitions are intended to apply throughout this application unless a contrary meaning is clearly indicated.

The microcrystalline cellulose, simply blended with propylene glycol alginate, provides important film characteristics required to provide an elegant coating which is particularly useful in, for example, coating pharmaceutical and veterinary tablets, caplets, granules, and spheres which contain active ingredients which require release promptly after being placed in aqueous media or ingested.

Microcrystalline cellulose is a purified, partially depolymerized cellulose that is generally produced by treating a source of cellulose, preferably alpha cellulose in the form of a pulp from fibrous plants, with a mineral acid, preferably hydrochloric acid. The acid selectively attacks the less ordered regions of the cellulose polymer chain, thereby exposing and freeing the crystallite sites, forming the crystallite aggregates which constitute microcrystalline cellulose. These are then separated from the reaction mixture and washed to remove degraded by-products. The resulting wet mass, generally containing 40 to 60 percent moisture, is referred to in the art by several names, including hydrolyzed cellulose, microcrystalline cellulose, microcrystalline cellulose wetcake, or simply wetcake. This microcrystalline cellulose wetcake may be used as such or may be further modified, for example, by attrition and/or drying, and utilized in accordance with the present invention.

Microcrystalline cellulose may also be produced for use in the present invention using a steam explosion treatment. In this process, wood chips or other cellulosic materials are placed in a chamber into which super-heated steam is introduced. After being maintained for a period of about 1–5 minutes, the exit valve is opened rapidly, releasing the contents explosively and yielding microcrystalline cellulose. No additional acid need be introduced into the reaction mixture, since it is believed that the acidic materials in the wood chips and the elevated temperature and pressure hydrolyze the cellulose and degrade it. In addition to the specific forms of microcrystalline cellulose, the present invention also contemplates the use of other cellulose derivatives, including microreticulated cellulose, also known as microreticulated microcrystalline cellulose, and powdered cellulose such as a commercial material sold as "Solka Floc®."

As discussed in greater detail below, the microcrystalline cellulose preferred for use in the present invention is microcrystalline cellulose which has an average particle size below about 100 microns, preferably microcrystalline cellulose which has been attrited or has an average particle size in the range of 1 to 50 microns, preferably 1 to 30 microns.

The microcrystalline cellulose and propylene glycol alginate may be blended in any suitable manner, such as dry blending. Dry blended microcrystalline cellulose, for example, Avicel® PH-105, average particle size 20 microns, and propylene glycol alginate have been found to provide coating compositions that are at least equal to, and in most cases, superior to coating compositions currently available commercially.

Propylene glycol alginate by itself is known to be a film forming hydrocolloid when an aqueous dispersion thereof is spread on a surface and allowed to dry. However, the film is considered to be too weak to provide a satisfactory coating. But, when a film forming amount thereof is blended with microcrystalline cellulose having, for example, a particle size below 100 microns, preferably in the range of about 1–50 microns, more preferably, about 1–30 microns and a strengthening polymer in accordance with the present invention, elegant, high performance coating formulations are provided.

For purposes of this invention, a film forming amount of propylene glycol alginate may be in the range of about 10% to about 50%, more specifically about 12% to about 50%, by dry weight of the coating composition. The propylene glycol alginate employed in the present invention may vary widely in viscosity. A typical high viscosity propylene glycol alginate is such that a 2% aqueous solution thereof has a viscosity in the range of 700 to 1800 mPa.s at 25° C., and is commercially available as Protonal® ester SD-LB, Pronova/FMC Corporation. A typical low viscosity propylene glycol alginate is such that a 2% aqueous solution thereof has a viscosity in the range of 20 –30 mPa.s at 25° C., and is commercially available as Profoam®, Pronova/FMC Corporation.

High viscosity propylene glycol alginate is generally employed in a lower amount than that employed for low viscosity material, typically in the range of 10% to about 20% by dry weight of the coating composition, as illustrated in examples 1–6 below. Use of substantially higher amounts of high viscosity propylene glycol alginate may result in coating solutions which are too viscous, tend to plug coating equipment, and may not flow sufficiently to form a satisfactory coating. Low viscosity propylene glycol alginate conversely is generally used in a higher amount, typically in the range of 20% to 50% by dry weight of the coating composition, as illustrated in examples 7 through 30.

Propylene glycol alginate may be used in combination with other film forming materials, for example, carrageenan and cellulosic polymers such as HPMC and hydroxypropylcellulose.

Carrageenan, preferably iota carrageenan, may suitably be employed as a multifunctional component in combination with propylene glycol alginate at a concentration in the range of about 3% to about 20% of the dry weight of the coating composition. When carrageenan is employed in the composition at a concentration in the range of about 3% to about 8%, it is believed to serve primarily to improve the gloss of the resulting coating, that is, as a gloss enhancer. When used for this purpose the weight ratio of propylene glycol alginate to carrageenan is suitably in the range of about 2:1 to about 10:1.

Carrageenan may also be used at a level above about 9%, for example, at a concentration in the range of about 9% to about 20%, more specifically in the range of 10% to about 15%. At these levels it is believed to serve not only to improve gloss of the coating, but also to contribute film forming properties and to contribute to the strength and integrity of the resulting film coating. Depending on the weight ratio of propylene glycol alginate to carrageenan, carrageenan may be viewed to function as a co-film-former or as a supplemental or secondary film-former in the coating compositions. Such a weight ratio of propylene glycol alginate to carrageenan may be in the range of 2:1 to about 0.8:1. For example, when the weight ratio of propylene glycol alginate to carrageenan is in the range of about 1.5:1 to about 2:1, propylene glycol alginate may be considered to be the primary film-former and carrageenan the secondary film-former, as illustrated in examples 18 through 21 and 25 through 30. When approximately equal amounts of propylene glycol alginate and carrageenan are employed, that is, when the propylene glycol alginate to carrageenan weight ratio is, for example, in the range of about 1:08 to about 1:1.2, each of them may be considered to contribute relatively equal film forming properties to the resulting film coating, thus are considered to be co-film-formers as illustrated by examples 18 and 20–24.

The weight ratio of microcrystalline cellulose to propylene glycol alginate in the compositions of this invention may vary depending on the application, but generally range from about 90:10 to about 20:80, more specifically from about 80:20 to about 20:80. A particular advantage for the dry, physical blends is that the ratio can be easily changed by simple blending techniques rather than manufacturing different ratios of a coprocessed material. Thus, the dry, physical blends provide great flexibility for specific applications having different requirements.

A dry, physical blend of microcrystalline cellulose and a film forming amount of propylene glycol alginate, a strengthening polymer, preferably, hydroxyethylcellulose (HEC), are present in the coating formulation of this invention, advantageously in combination with other optional ingredients such as a plasticizer, a surfactant, a filler or a coloring agent, other conventional excipients or combinations thereof. Other strengthening polymers which can provide the same benefit and may be used instead of HEC include HPMC, hydroxypropylcellulose, ethylcellulose, methylcellulose and polyvinylpyrrolidone (PVP), however care must be exercised in the use of such alternative materials to avoid retarding release of active ingredients and/or bioavailability.

The preferred amount of strengthening polymer is less than the total amount of microcrystalline cellulose and propylene glycol alginate present in the composition. Depending on the desired hardness of the coating, the strengthening polymer may be employed in the composition at a level of about 0.5% to about 30%, advantageously about 5% to 30% to provide strength and improved appearance to the coating. This strength can be demonstrated by casting films of coating formulations on a flat, non-adherent surface, cutting strips of uniform width from the casting, and subjecting the strips to tensile testing on, for example, an Instron Tensile Tester. The results of these tests show a very significant increase in tensile strength and decreased brittleness of the film when HEC or another strengthening polymer is included in the formulation. Strengthening polymers suitable for use in this invention, which will not retard release from tablets or other solid dosage forms, are those polymers having a viscosity equal to or less than 20 mPa.s in a 2% aqueous solution at 20° C. When a strengthening polymer is employed in the composition in absence of a plasticizer, it is generally employed at about 15% to about 30% by dry weight coating composition, and HEC is preferably employed at about 20% to about 25% by dry weight of the formulation.

In addition to the foregoing ingredients, the compositions of this invention may also contain at least one of a plasticizer, a surfactant, a filler, a coloring agent or a combination of these additional components of the composition. Thus, a conventional plasticizer may also be included in the coating composition. Suitable plasticizers include polyethylene glycol, triacetin, dibutyl sebacate, propylene glycol, sorbitol, glycerin, and triethyl citrate. Of these, triacetin is preferred. These plasticizers may be employed in the coating compositions of the invention at about 18% to about 36% by dry weight of the coating composition, advantageously about 20% to about 30% by dry weight of the coating composition.

Fillers suitable for use in the compositions of the invention include, for example, calcium carbonate, dicalcium phosphate and carbohydrates, such as starch, maltodextrin, lactose, mannitol and other sugars or croscarmellose sodium. Of these, mannitol or maltodextrin is a preferred filler. Surfactants which are either anionic or nonionic may be used beneficially in the edible, hardenable coating compositions of the present invention. Useful surfactants may be, for example, sodium lauryl sulfate, hydroxylated soy lecithin, polysorbates, and block copolymers of propylene oxide and ethylene oxide. Coloring agents and opacifiers which may be used in these coatings or added to a suspension thereof include aluminum lakes, insoluble pigments, water soluble dyes, titanium dioxide, and talc. Stearic acid or a salt or ester thereof, may be included at a level of about 1% to about 5% by dry weight of the compositions to increase gloss of the coating, particularly when a plasticizer is not employed in the composition.

A coating formulation of this invention may be sold as a dry powder formulation or as a ready-to-use dispersion in water. For aqueous dispersions it is preferred that these be prepared under aseptic conditions. Heating the water to an elevated temperature, for example, 85° C., prior to preparation of the dispersion has shown that bacteria, mold, and yeast growth are prevented for at least 48 hours on agar pour plates. Therefore, if the containers for the dispersion are properly sanitized and then kept closed after being filled until the dispersion is used, there is little likelihood of bacteria, mold, or yeast growing in the dispersion. Alternatively, if a formulation is to be sold as an aqueous dispersion to be stored for a period of time, a preservative may be added. A combination of methyl and/or propyl paraben has been found to be useful in this regard.

On a dry weight percentage basis the composition of this invention comprises from about 15% to about 50% of microcrystalline cellulose, about 10% to about 50% by weight of propylene glycol alginate, and about 5% to about 25% of strengthening polymer. If a plasticizer is employed, it is advantageously used at about 20% to about 30% by weight of the composition. The composition of the invention may also include an inert filler at about 2% to about 28% by weight. Optionally, about 1% to about 30% by weight of the formulation may comprise edible coloring agents and opacifiers such as talc or titanium dioxide, including from 1% to about 8% of coloring component such as a food dye or pigment, preferably about 1% to about 3%. Other optional ingredients may include a surfactant at about 0.5% to about 10%, advantageously 0.5 to about 7%, preferably 1.25% to 3% when a filler such as mannitol is present. When no filler is employed higher amounts of surfactants such as lecithin may be employed at a level of about 3% to about 20%. Preservatives, such as methyl paraben at 0.75% to 1.50% and/or propyl paraben at 0.075% to 0.15% may also be present in the formulation.

The low level of fillers present in these coating formulations, particularly when the opacifier is titanium dioxide, enables the formulator to utilize relatively small amounts of coloring agent. Since coloring agents are quite costly, this provides a significant cost reduction from those formulation requiring from 6% to about 16% to effectively color prior art coating formulations.

The viscosity of the hydrated formulation can be important. It ideally should be low enough to be pumped to a spray unit continuously and then sprayed evenly in a useful pattern onto the substrate being coated. A useful concentration of the dry ingredients in water on a weight percentage basis, therefore, may be about 6% to about 15%, advantageously 6.5% to 11%, preferably about 8% to about 11%. To assure uniformity of the coating composition, it may be preferable to maintain agitation of the aqueous dispersion during the entire period of its being sprayed onto the pharmaceutical or veterinary solid dosage forms, confectionery, seeds, animal feed, fertilizer, pesticide tablets, or food.

The preferred edible, hardenable, prompt release coating formulations of this invention may generally be prepared and used according to a simple procedure. A dry blend of microcrystalline cellulose and propylene glycol alginate, and a strengthening polymer, such as hydroxyethylcellulose, and optionally at least one additional ingredient, such as polyethylene glycol or other acceptable plasticizer, optionally together with a solid filler such as maltodextrin, lactose, mannitol or the like, preservatives, and/or surfactants are blended to form dry coating composition. Addition of edible coloring agents, for example, a water soluble dye or a pigment, may precede the hydration step required to prepare the final coating formulation. This dry mixture is then added slowly to the vortex of stirred, purified water. Stirring of this mixture is continued for a sufficient period to allow all of the components to be fully hydrated. If a colored coating material is required a water soluble dye or a pigment may also be added, preferably as a dispersion or solution, to the hydrated coating composition. Optionally surfactants, and/ or plasticizers may also be added at this stage of the process.

In the formulations of microcrystalline cellulose and propylene glycol alginate, a simple propeller mixer provides adequate agitation for rapid hydration. The period of hydration may be as short as 0.5 hours. It may, and preferably should, be longer, but more than 3 hours is not believed to be necessary. Hydration can take place at room temperature or at elevated temperatures as high as 65.5° C. (150° F.), preferably at a temperature about 48.9° C. (120° F.). The time required for full hydration and the viscosity of the dispersion are both considerably reduced when the dispersion is prepared at an elevated temperature, but coating dispersions prepared at ambient temperature only require an increase in hydration time and a slight reduction in solids content to perform completely satisfactorily. As previously stated, these formulations may be prepared on the day preceding the coating operation, if that is more convenient; however, a period of mixing will be required to overcome the thixotropic behavior of a formulation which sets up during overnight storage. Unlike coating formulations based primarily on hydroxyalkyl ethers of cellulose, for example, HPMC, constant stirring of the microcrystalline and propylene glycol alginate-based formulations of this invention does not need to be continued throughout the coating procedure, but mixing may continue, if preferred.

Any commercial spray coater may be used to apply the coating. Examples of useful coaters are Vector High Coaters manufactured by Vector Corporation and Accela-Cota manufactured by Thomas Engineering. Equipment variables which one skilled in the art can manipulate to provide an elegant coating based on dry blends of microcrystalline cellulose and propylene glycol alginate, include inlet temperature, outlet temperature, air flow, speed of rotation of the coating pan, and the rate at which the coating formulation is pumped to the coater. It is important that the inlet and outlet temperatures be controlled so that they are high enough to efficiently dry the coating to prevent the tumbling action of the already-coated tablets from damaging the newly-applied coating before more coating is applied to the same tablets.

Hydroxyethylcellulose binds water more effectively than propylene glycol alginate does. Thus, the presence of the major amount propylene glycol alginate in the formulations of this invention has a significant effect on the speed of drying of the edible coatings. Drying times are reduced considerably because of the presence of the propylene glycol alginate which dilutes the negative effect of HEC on drying time. Thus, in the case of low melting active pharmaceutical agents, for example, ibuprofen, the outlet temperature can be reduced and still provide short enough drying time to be commercially useful.

Hydroxyethylcellulose is particularly susceptible to clogging spray nozzles at high temperatures. An additional benefit provided by the formulations of this invention is the avoidance of clogging of the spray nozzles with dispersions being sprayed at high temperatures.

The level of coating applied to pharmaceutical or veterinary dosage forms is preferably between about 0.5% to about 4% by weight of the uncoated dosage form, more preferably about 2% to about 3.5%, by weight of the uncoated dosage form. This level of coating will provide an elegant, serviceable coating to a wide variety of dosage forms. To apply a heavier coating to tablets would not be economical, and it might adversely affect disintegration of the tablets or other properties. Too light a coating would not provide optimal properties normally expected from a coating, for example, improved friability or adequate taste masking.

For confections the coating level should be about 5% to about 10% by weight of the uncoated confection. Seed coatings should be in the range of about 3% to about 6% by weight of the uncoated seeds. Fertilizers and pesticide tablets and granules benefit from coating of 1% to about 3%, by weight of the uncoated granules or tablets.

From the following examples is has been shown that the coatings of the present invention may be applied successfully to tablets having a wide variety of active ingredients incorporated therein. For example, it has been reported that multivitamin tablets are difficult to coat because of the lipophilic surface properties of the vitamins. Similarly, ibuprofen is a challenging active ingredient to coat. Tablets comprising both of these difficult-to-coat active ingredients have been coated readily with the instant invention, providing elegant tablets. Additionally, the coatings have been applied to tablets which have been debossed with letters or a logo without bridging which would hide, or even obliterate, the debossed design.

An additional utility of the coating formulations of this invention is as a replacement for sugar coating of tablets. A sugar coating is applied primarily to increase the weight and/or size of the tablet, but this is an old art which presents numerous problems. It is, therefore, desirable to replace the traditional sugar coating with a more easily applied coating. This coating procedure has the additional advantage that no topcoat is required to be applied as it is done with a sugar coating.

Storage of coated tablets under ambient temperature and humidity and 40° C. and 75% relative humidity for one to three months has demonstrated that no significant degradation has occurred. These tablets have disintegrated within the same length of time as the same batch of newly coated tablets did, and in each case provided dissolution rates and times substantially equal to those of the uncoated tablets used as a substrate for coating. This is an additional unexpected benefit of the coatings based on propylene glycol alginate and microcrystalline cellulose, and it differs from the known drawbacks of coating formulations in which HPMC is the primary or only film-former.

All components of the formulation are typically pharmaceutically acceptable, edible food grade materials.

The following examples, in which percentages are weight percent and tablet hardness is in Kiloponds (Kp), are provided to demonstrate the method of preparation and application of these elegant coatings, but they are not intended to be limiting as to amounts and the type of optional ingredients or the specific method of application of the tablet coating described herein.

EXAMPLE 1

In a Patterson-Kelly twin shell blender were placed 48.0 grams of a blend of microcrystalline cellulose (Avicel® PH-105, 35 grams) and propylene glycol alginate (13 grams), 20 grams of hydroxyethylcellulose (Aqualon®250L), 25 grams of triacetin, and 3 grams of Pluronic F-68 (BASF). After the dry components had been thoroughly blended, the blend was added slowly to the vortex of 1011.1 grams deionized water which was stirred with a Lightnin' mixer. The suspension was stirred for 2 hours at ambient temperature to fully hydrate the composition. To this dispersion was added 4.0 grams of red #40 liquid dispersion (Crompton and Knowles). A Vector High Coater LDCS was charged with 1 Kg of each of acetaminophen tablets and ibuprofen caplets. The coater was operated at an inlet temperature of 84–85° C., an outlet temperature of 40–45° C., and 14–15 rpm. During the spraying, which required 56 minutes, a 3 weight percent coating, based on the weight of the tablets & caplets was applied. Friability of the tablets and caplets was 0% after 10 minutes.

EXAMPLES 2 THROUGH 5

By the method of Example 1, the dry components of each formulation were dry blended and dispersed in deionized water after which the triacetin and liquid components were added to the dispersion. The dispersion was then sprayed on caplets which were tested for friability. These examples are summarized in Table 1 below:

TABLE 1

| Example: | 2 | 3 | 4 | 5 |
|---|---|---|---|---|
| Ingredients | Weight (grams) | | | |
| Avicel PH-105 | 37 | 35 | 37 | 37 |
| Hydroxyethylcellulose | 22 | 20 | 22 | 22 |
| PGA[a] | 13 | 13 | 12 | 12 |
| Pluronic F-68 | 3.5 | 3 | — | 1.5 |
| Red #40 dispersion | 24.5 | 4 | 6 | 7.5 |
| Triacetin | — | 25 | — | — |
| Mannitol[b] | — | — | 18 | 15 |
| Iota carrageenan | — | — | 5 | 5 |
| Deionized water | 1011.1 | 1011.1 | 1011.1 | 1011.1 |
| Hydration time | 2 hours | >1 hour | 6 hours | >1 hour |
| Caplets | Charge (Kg) | | | |
| Acetaminophen | 0.67 | 1 | 0.67 | 0.67 |
| Ibuprofen | 0.67 | 1 | 0.67 | 0.67 |
| Chlorpheniramine | 0.67 | — | 0.67 | 0.67 |
| Spray conditions | | | | |
| Inlet temperature | 84–89° C. | 83–85° C. | 63–69° C. | 69–74° C. |
| Outlet temperature | 36–40° C. | 40–42° C. | 38–39° C. | 30–32° C. |
| Drum speed | 14–15 rpm | 15 rpm | 11 rpm | 10 rpm |
| Time | 54 minutes | 57 minutes | 55 minutes | 58 minutes |
| Coating weight (%) | 3 | 3 | 3 | 3 |
| Friability (10 minutes) | | | | |
| Acetaminophen | 0% | 0% | 0% | NT |
| Ibuprofen | 0% | 0% | slight | NT |
| Chlorpheniramine | NT[c] | — | NT | NT |

[a]Polypropylene glycol alginate (Protonal ® ester SD-LB, Pronova)
[b]Granular mannitol
[c]NT = not tested

EXAMPLE 6

The components of this example were dry blended. The dry blend was dispersed in deionized water, then sprayed on caplets and/or tablets which were tested for friability. This example is summarized in Table 2:

TABLE 2

| Example: | 6 |
|---|---|
| Ingredients | Weight (grams) |
| Avicel PH-105 | 37 |
| PGA[a] | 13 |
| Iota carrageenan | 5 |
| Hydroxyethylcellulose | 22 |
| Mannitol[b] | 17.5 |
| Pluronic F-68 | 3.5 |
| Blue Lake #2 | 2 |
| Deionized water | 1150 |
| Hydration time | 2 hours |
| Caplets | Charge (Kg |
| Ibuprofen | 1 |
| Chlorpheniramine | 1 |
| Spray conditions | |
| Inlet temperature | 97–99° C. |
| Outlet temperature | 31–35° C. |
| Drum speed | 12–13 rpm |
| Time | 62 minutes |
| Coating weight % | 3% |

TABLE 2-continued

| Example: | 6 |
|---|---|
| Friability (10 minutes) | |
| Ibuprofen | 0% |
| Chlorpheniramine | 0% |

[a] Polypropylene glycol alginate (Protonal ® ester SD-LB, Pronova)
[b] Granular mannitol

EXAMPLES 7–13

By the method of Example 1, the dry components of each formulation were dry blended then dispersed in deioized water. The dispersion was then hydrated and sprayed on caplets which were tested for friability, gloss and disintegration time. The examples are summarized in Table 3 below.

EXAMPLES 14–30

These additional examples were also prepared and applied in the manner of Examples 7–14. The resulting coating compositions are set forth in Table 4 below.

TABLE 3

| Example | 7 | 8 | 9 | 10 | 11 | 12 | 13 |
|---|---|---|---|---|---|---|---|
| Ingredients | | | Percentage by weight | | | | |
| Avicel PH105 | 20 | 20 | 15 | 20 | 25 | 20 | 25 |
| PGA[a] | 30 | 40 | 50 | 40 | 30 | 30 | 35 |
| HEC | 20 | 10 | 5 | — | — | 15 | 15 |
| Lecithin[b] | 3 | 3 | 3 | — | 3 | 3 | 3 |
| Maltodextrin M180 | 17 | 17 | 17 | 25 | 22 | 17 | 17 |
| Iota Carrageenan | 5 | 5 | 5 | 5 | 5 | 5 | 5 |
| Red hydrophilic Iron Oxide | 5 | 5 | 5 | — | 15 | 10 | — |
| Blue lake/Yellow lake blend | — | — | — | 10 | — | — | — |
| % Solids | 8 | 8 | 8 | 8 | 8 | 8 | 9 |
| Caplets | | | | Charged (Kg) | | | |
| Acetominophen | 2 | 2 | 12 | 12 | 12 | 12 | 12 |
| Inlet Temperature (° C.) | 78–88 | 67–90 | 46–53 | 50–53 | 52–54 | 52–54 | 67–72 |
| Exhaust Temperature (° C.) | 35–41 | 29–36 | 33–36 | 32–38 | 32–36 | 34–36 | 30–35 |
| RPM | 13 | 15 | 9 | 9 | 9 | 8 | 13 |
| Spray Rate (gm/ml) | 12 | 19 | 55 | 66 | 72 | 67 | 11 |
| Time (minutes) | 70 | 41 | 84 | 85 | 64 | 66 | 59 |
| Coating weight (%) | 3 | 3 | 3 | 3 | 3 | 3 | 3 |
| Appearance (shine)[d] | 5 | 4 | 4 | 2 | 3 | 4 | 4 |
| Friability (% - 10 minutes) | 0 | 0 | 0 | MC[c] | MC[c] | 0 | 0 |
| Disintegration Time, 37° C. (minutes) | <5 | <5 | <5 | <12 | <5 | <5 | |

[a] Low viscosity propylene glycol alginate (Profoam ®, Pronova)
[b] Hydroxylated soy lecithin
[c] Minor Chipping
[d] 5 = superior, 4 = acceptable; 3 = marginal; 2 = poor

TABLE 4

| | (%) By Weight | | | | | | | | | | | | | | | | |
|---|---|---|---|---|---|---|---|---|---|---|---|---|---|---|---|---|---|
| Example: | 14 | 15 | 16 | 17 | 18 | 19 | 20 | 21 | 22 | 23 | 24 | 25 | 26 | 27 | 28 | 29 | 30 |
| Ingredients | | | | | | | | | | | | | | | | | |
| Avicel PH-105 | 25 | 20 | 25 | 20 | 34 | 25 | 20 | 20 | 25 | 25 | 25 | 25 | 25 | 22 | 25 | 25 | 25 |
| PGA[a] | 35 | 35 | 35 | 30 | 13 | 26 | 25 | 25 | 13 | 13 | 13 | 20 | 18 | 26 | 20 | 15 | 20 |
| Hydroxyethyl-cellulose | 15 | 15 | 17 | 20 | 22 | 22 | 20 | 20 | 20 | 20 | 20 | 17 | 15 | 20 | 15 | 20 | 20 |
| Iota carrageenan | 5 | 5 | 5 | 5 | 12 | 12 | 12 | 12 | 15 | 15 | 15 | 12 | 12 | 12 | 12 | 10 | 10 |
| Lecithin[b] | 3 | 3 | 5 | 3 | 7 | 3 | 3 | 3 | 7 | 7 | 5 | | 7 | 3 | 7 | 3 | 5 |
| Maltodextrin | 3 | 3 | 3 | | 3 | 3 | 3 | 3 | | 3 | | | 3 | 3 | 3 | 3 | 3 |
| PIGMENT (Var) | 5 | 10 | 10 | 5 | 5 | 7 | 10 | 10 | 5 | 7 | 7 | 7 | 5 | 8 | 8 | 10 | 10 |
| Mannitol[c] | 9 | 9 | — | 17 | 4 | 2 | 7 | | | 10 | 10 | 6 | 10 | 3 | — | — | — |
| Lactose | | | | | | | | | 15 | | | | | | | | |
| Croscarmellose | | | | | | | | | | | | 5 | 3 | 5 | 3 | 5 | 3 | 2 |
| Calcium carbonate | | | | | | | | 7 | | | | 7 | — | | | | |
| dicalcium Phosphate | | | | | | | | | | | | | | | 5 | 11 | 5 |
| PVP 29/32,25,s603 | | | | | | | | | | | | | | | | | |

[a] Low Viscosity propylene glycol alginate (Profoam ®, Pronova)
[b] Hydroxylated soy lecithin
[c] Granular mannitol

What is claimed is:

1. An edible, hardenable, prompt release, pharmaceutical and veterinary solid dosage form coating composition comprising (a) microcrystalline cellulose having an average particle size less than 100 microns, (b) a film forming amount of propylene glycol alginate, (c) a strengthening polymer and optionally (d) at least one of a plasticizer, a surface active agent and a filler, wherein the weight ratio of microcrystalline cellulose to propylene glycol alginate is in the range of 90:10 to 20:80 wherein said prompt release, pharmaceutical and veterinary solid dosage form coating composition does not, when ingested or placed in aqueous media, adversely retard release or dissolution of active ingredients from a pharmaceutical or veterinary solid dosage form to which said coating composition is applied.

2. The coating composition of claim 1, comprising 5% to 50% by weight microcrystalline cellulose, 10% to 50% by weight propylene glycol alginate, and 5% to 25% by weight strengthening polymer.

3. The coating composition of claim 2, comprising 12% to 50% by weight propylene glycol alginate.

4. The coating composition of claim 1 in which the strengthening polymer is hydroxyethylcellulose.

5. The coating composition of claim 4, further comprising from 20% to 30% by weight plasticizer.

6. The coating composition of claim 5, in which the plasticizer is triacetin.

7. The coating composition of claim 4, further comprising from 1% to 5% by weight surface active agent.

8. The coating composition of claim 4, further comprising from 10% to 30% by weight of a filler.

9. The coating composition of claim 8, in which the filler is at least one of mannitol or maltodextrin.

10. The coating composition of claim 1, wherein the microcrystalline cellulose has an average particle size in the range of 1 to 50 microns.

11. The coating composition of claim 1, further comprising carrageenan in an amount of from 3% to 20% by dry weight of the composition.

12. The coating composition of claim 11, wherein carrageenan is present in an amount in the range of 3% to 8% by dry weight of the composition and the weight ratio of propylene glycol alginate to carrageenan is in the range of 2:1 to 10:1.

13. The composition of claim 11 wherein carrageenan is present in an amount in the range of 9% to 20% by dry weight of the composition and the weight ratio of propylene glycol alginate to carrageenan is in the range of 2:1 to 0.8:1.

14. The coating composition of claim 1, wherein said composition is a dry blend.

15. The coating composition of claim 1, wherein said composition is an aqueous dispersion.

16. The coating composition of claim 1 further comprising a coloring agent.

17. A solid dosage form coated with the composition of claim 1.

18. A method for forming an edible, hardenable, prompt release, pharmaceutical and veterinary solid dosage form coating composition comprising:
   i) combining (a) microcrystalline cellulose having an average particle size less than 100 microns, (b) a film forming amount of propylene glycol alginate, (c) a strengthening polymer and optionally (d) at least one of a plasticizer, a surface active agent and a filler, wherein the weight ratio of microcrystalline celulosemto proplyene glycol alginate is in the rande og 9010 20:80; and
   ii) forming a film coating by spraying an aqueous suspension of i) onto a pharmaceutical or veterinary solid dosage form,
   wherein said prompt release, pharmaceutical and veterinary solid dosage form coating composition does not, when ingested or placed in aqueous media, adversely retard release or dissolution of active ingredients from said pharmaceutical or veterinary solid dosage form to which said coating composition is applied.

19. A method of coating pharmaceutical and veterinary solid dosage forms comprising the steps of hydrating the coating composition of claim 1, followed by spray coating said hydrated coating composition onto a pharmaceutical or veterinary solid dosage form.

20. An edible, hardenable, prompt release, pharmaceutical and veterinary solid dosage form coating composition comprising (a) microcrystalline cellulose, (b) a film forming amount of propylene glycol alginate, (c) a strengthening polymer and optionally (d) at least one of a plasticizer, a surface active agent and a filler, wherein the weight ratio of microcrystalline cellulose to propylene glycol alginate is in the range of 90:10 to 20:80 and wherein said prompt release, pharmaceutical and veterinary solid dosage form coating composition does not, when ingested or placed in aqueous media, adversely retard release or dissolution of active ingredients from a pharmaceutical or veterinary solid dosage form to which said coating composition is applied.

* * * * *